(12) United States Patent
Johnson et al.

(10) Patent No.: US 6,759,381 B1
(45) Date of Patent: Jul. 6, 2004

(54) AZEOTROPE-LIKE COMPOSITIONS OF 1-CHLORO-1,3,3,3-TETRAFLUOROPROPANE AND 1,2-DICHLORO-3,3,3-TRIFLUOROPROPENE

(75) Inventors: Robert C. Johnson, Lancaster, NY (US); Daniel C. Merkel, West Seneca, NY (US); Hsuehsung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/430,078

(22) Filed: May 6, 2003

(51) Int. Cl.$^7$ .................................................. C11D 7/30
(52) U.S. Cl. ........................ 510/408; 510/411; 510/412; 510/415; 570/101; 570/123; 570/170; 570/178
(58) Field of Search ................................ 510/408, 411, 510/412, 415; 570/101, 123, 170, 178

(56) References Cited

U.S. PATENT DOCUMENTS

| | | | |
|---|---|---|---|
| 5,574,192 A | 11/1996 | VanDerPuy et al. | ........ 570/167 |
| 6,001,796 A | 12/1999 | Pham et al. | ................. 510/408 |
| 6,060,629 A | 5/2000 | Pham et al. | ................. 570/178 |
| 6,365,566 B1 | 4/2002 | Bogdan et al. | ............. 510/411 |
| 6,475,971 B2 * | 11/2002 | Pham et al. | ................. 510/408 |
| 6,500,795 B2 | 12/2002 | Pham et al. | ................. 510/412 |
| 6,514,928 B1 | 2/2003 | Bement et al. | ............. 510/415 |
| 6,518,467 B2 | 2/2003 | Tung et al. | ................. 570/171 |
| 6,524,496 B2 | 2/2003 | Cook et al. | ................... 252/67 |
| 6,534,467 B2 | 3/2003 | Pham et al. | ................. 510/408 |

* cited by examiner

*Primary Examiner*—Yogendra N. Gupta
*Assistant Examiner*—Eisa Elhilo
(74) *Attorney, Agent, or Firm*—Colleen D. Szuch

(57) ABSTRACT

Provided are azeotropic and azeotrope-like mixtures of 1-chloro-1,3,3,3-tetrafluoropropane and 1,2-dichloro-3,3,3-trifluoropropene that are useful as an intermediate in the production of HFC-245fa. HFC-245fa is useful as a nontoxic, zero ozone depleting fluorocarbon useful as solvents, blowing agents, refrigerants, cleaning agents, aerosol propellants, heat transfer media, gaseous dielectrics, fire extinguishing compositions and power cycle working fluids.

33 Claims, No Drawings

US 6,759,381 B1

AZEOTROPE-LIKE COMPOSITIONS OF 1-CHLORO-1,3,3,3-TETRAFLUOROPROPANE AND 1,2-DICHLORO-3,3,3-TRIFLUOROPROPENE

BACKGROUND OF THE INVENTION

The present invention relates to azeotropic and azeotrope-like compositions of 1-chloro-1,3,3,3-tetrafluoropropane and 1,2-dichloro-3,3,3-trifluoropropene, or more particularly to such azeotropic and azeotrope-like compositions useful as intermediates in the production of 1,1,1,3,3-pentafluoropropane, and as refrigerants, blowing agents and solvents.

Traditionally, chlorofluorocarbons (CFCs) like trichlorofluoromethane and dichlorodifluoromethane have been used as refrigerants, blowing agents and diluents for gaseous sterilization. However, these materials are undesirable because they contribute to the depletion of the ozone layer. Therefore, stratospherically safer alternatives to these materials are desirable.

In recent years there has been universal concern that completely halogenated chlorofluorocarbons might be detrimental to the Earth's ozone layer. Consequently, there is a worldwide effort to use fluorine-substituted hydrocarbons which contain fewer or no chlorine substituents. Accordingly, the production of HFC's, or compounds containing only carbon, hydrogen and fluorine, has been the subject of interest to provide environmentally desirable products for use as solvents, blowing agents, refrigerants, cleaning agents, aerosol propellants, heat transfer media, dielectrics, fire extinguishing compositions and power cycle working fluids. In this regard, 1,1,1,3,3-pentafluoropropane (HFC-245fa), a hydrofluorocarbon (HFC) having zero ozone depletion potential, is considered as a replacement for chlorofluorocarbons such as dichlorodifluoromethane in refrigeration systems and trichlorofluoromethane as a blowing agent. It is known in the art to produce HFC's by reacting hydrogen fluoride with various hydrochlorocarbon compounds. For example, HFC-245fa is well known in the art and is described in U.S. Pat. Nos. 5,496,866 and 5,574,192, which are herein incorporated by reference.

An important intermediate in the production of HFC-245fa is the partially substituted intermediate 1-chloro-1,3,3,3-tetrafluoropropane (HCFC-244fa). It has now been found that purification of this intermediate is complicated by the presence of an azeotrope or azeotrope-like mixture of 1-chloro-1,3,3,3-tetrafluoropropane and 1,2-dichloro-3,3,3-trifluoropropene (HCFC-1223xd). This is despite the rather wide disparity of the normal boiling points of these two compounds (HCFC-244fa boils at about 43° C., while HCFC-1223xd boils at about 53° C.). This composition, once formed, may thereafter be separated into its component parts by extraction techniques or reaction techniques.

DESCRIPTION OF THE INVENTION

The invention provides an azeotropic or azeotropic-like composition comprising 1-chloro-1,3,3,3-tetrafluoropropane and 1,2-dichloro-3,3,3-trifluoropropene.

The invention also provides a process for forming an azeotropic or azeotropic-like composition of 1,2-dichloro-3,3,3-trifluoropropene (HCFC-1223xd) and 1-chloro-1,3,3,3-tetrafluoropropane (HCFC-244fa) comprising the steps of:

(a) reacting hydrogen fluoride with 1,1,1,3,3-pentachloropropane (HCC-240fa) thereby producing an intermediate composition; and thereafter (b) separating an azeotropic or azeotropic-like composition of 1,2-dichloro-3,3,3-trifluoropropene (HCFC-1223xd) and 1-chloro-1,3,3,3-tetrafluoropropane (HCFC-244fa) from the intermediate composition.

In a method of preparing HFC-245fa, 1,1,1,3,3-pentachloropropane (HCC-240fa), is fluorinated with hydrogen fluoride (HF). The intermediate reaction products of this reaction include HFC-245fa, unreacted HF, hydrochloric acid, 1-chloro-1,3,3,3-tetrafluoropropane (HCFC-244fa), and 1,2-dichloro-3,3,3-trifluoropropene (HCFC-1223xd), and other intermediates and by-products. Upon removal of the by-products, including the removal of HFC-245fa, an azeotrope or azeotrope-like composition of HCFC-244fa and HCFC-1223xd is formed. This azeotrope or azeotrope-like composition is then available for separation into its component parts. The azeotropic or azeotrope-like composition may also be recycled to a fluorination reactor.

In particular, from about 5 moles to about 50 moles of hydrogen fluoride, more preferably from about 6 moles to about 30 moles of HF, and most preferably from about 7 moles to about 20 moles of HF, is reacted with about 1 mole of 1,1,1,3,3-pentachloropropane (HCC-240fa). The reaction is conducted at a temperature of from about 30° C. to about 200° C., more preferably from about 50° C. to about 180° C., and most preferably from about 70° C. to about 170° C. at a pressure of from about 15 psia to about 465 psia, more preferably from about 25 psia to about 265 psia and most preferably from about 30 psia to about 215 psia.

The result is an intermediate composition comprising 1,1,1,3,3-pentafluoropropane (HFC-245fa), unreacted hydrogen fluoride and hydrochloric acid (HCl), 1,2-dichloro-3,3,3-trifluoropropene (HCFC-1223xd) and 1-chloro-1,3,3,3-tetrafluoropropane(HCFC-244fa). Residual hydrogen fluoride, hydrochloric acid, and at least part of said 1,1,1,3,3-pentafluoropropane and other by-products are removed from the intermediate composition by purification methods, such as distillation, thereby leaving a remainder. The remainder is then distilled to remove any remaining 1,1,1,3,3-pentafluoropropane leaving an azeotropic or azeotrope-like composition of HCFC-244fa, and HCFC-1223xd. The distilling steps may be conducted at a pressure of from about 1 psia to about 250 psia, more preferably from about 15 psia to about 150 psia, and most preferably from about 20 psia to about 80 psia. The distilling steps may be conducted at a temperature of from about 30° C. to about 160° C., more preferably from about 35° C. to about 120° C. and most preferably from about 41° C. to about 97° C.

The thermodynamic state of a fluid is defined by its pressure, temperature, liquid composition and vapor composition. For a true azeotrope-like composition, the liquid composition and vapor phase are essentially equal at a given temperature and pressure range. In practical terms this means that the components cannot be separated during a phase change. For the purpose of this invention, an azeotrope-like composition means that the composition behaves like a true azeotrope in terms of its constant boiling characteristics and tendency not to fractionate upon boiling or evaporation. During boiling or evaporation, the liquid composition changes only slightly, if at all. This is in contrast with non-azeotrope-like compositions in which the liquid and vapor compositions change substantially during evaporation or condensation. One way to determine whether a candidate mixture is azeotrope-like within the meaning of this invention, is to distill a sample of it under conditions which would be expected to separate the mixture into its separate components. If the mixture is a non-azeotrope or non-azeotrope-like, the mixture will fractionate, i.e. separate into its various components with the lowest boiling component distilling off first, and so on. If the mixture is azeotrope-like, some finite amount of the first distillation cut will be obtained which contains all of the mixture components and which is constant boiling or behaves like a single substance. Another characteristic of azeotrope-like compositions is that there is a range of compositions containing the same components in varying proportions which are azeotrope-like. All such compositions are included by the term azeotrope-like as used herein. As an example, it is well known that at different pressures the composition of a given azeotrope will vary at least slightly as does the boiling point of the composition. Thus an azeotrope of two components represents a unique type of relationship but with a variable composition depending on the temperature and/or pressure. As is well known in the art, the boiling point of an azeotrope will vary with pressure.

As used herein, an azeotrope is a liquid mixture that exhibits a maximum or minimum boiling point relative to the boiling points of surrounding mixture compositions. An azeotrope or an azeotrope-like composition is an admixture of two or more different components which, when in liquid form under a given pressure, will boil at a substantially constant temperature, which temperature may be higher or lower than the boiling temperatures of the components and which will provide a vapor composition essentially identical to the liquid composition undergoing boiling. For the purpose of this invention, azeotrope-like compositions are defined to include azeotropic compositions and compositions that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotrope-like composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The invention provides a composition which comprises effective amounts of HCFC-244fa and HCFC-1223xd to form an azeotropic or azeotrope-like composition. By effective amount is meant an amount of each component which, when combined with the other component, results in the formation of an azeotrope or azeotrope-like composition. The inventive compositions preferably are binary azeotropes which comprise combinations of HCFC-244fa with HCFC-1223xd.

The azeotropic or azeotrope-like compositions of the invention have greater than about 0 to about 50 weight percent 1,2-dichloro-3,3,3-trifluoropropene and about 50 to less than about 100 weight percent 1-chloro-1,3,3,3-tetrafluoropropane. In a preferred embodiment, the compositions have from about 1 to about 50 weight percent of 1,2-dichloro-3,3,3-trifluoropropene and from about 50 to about 99 weight percent of 1-chloro-1,3,3,3-tetrafluoropropane. In a more preferred embodiment, the compositions having from about 1 to about 4 weight percent 1,2-dichloro-3,3,3-trifluoropropene and about 96 to about 99 weight percent 1-chloro-1,3,3,3-tetrafluoropropane. In a most preferred embodiment, the compositions have about 3.5 weight percent 1,2-dichloro-3,3,3-trifluoropropene and about 96.5 weight percent 1-chloro-1,3,3,3-tetrafluoropropane. The azeotrope or azeotrope-like compositions of the invention have a boiling point of from about 41° C. to about 160° C. at a pressure of from about 14 psia to about 215 psia. More particularly, such have a boiling point of about 41° C. to about 100° C. at a pressure of about 15 psia to about 80 psia. The most preferred azeotropic or azeotrope-like composition has been found to have a boiling point of about 96.5° C. at a pressure of about 78 psia. The boiling point at atmospheric pressure is about 41° C. The azeotropic or azeotrope-like composition contains about 3.5% of 1,2-dichloro-3,3,3-trifluoropropene at these temperatures and pressures.

The following non-limiting examples serve to illustrate the invention.

EXAMPLE 1

In the preparation of HFC-245fa, approximately 400 pounds of antimony pentachloride catalyst was charged into a 50 gallon reactor. The reactor temperature was raised to about 95° C. About 25 lbs/hr of HCC-240fa, 15 lbs/hr of HF and 2 lbs/hr of $Cl_2$ were fed to the reactor continuously, with the $Cl_2$ keeping the catalyst active. The reactor pressure was maintained at about 215 psia. The product stream contained HFC-245fa, HF, HCl and small amounts of organic by-products, including 1,2-dichloro-3,3,3-trifluoropropene (HCFC-1223xd) and 1-chloro-1,3,3,3-tetrafluoropropane (HCFC-244fa). Next, unreacted HF and HCl were removed, along with most of the HFC-245fa, leaving a mixture of by-products. A distillation of these byproducts was performed, from which a lights cut was retained, containing primarily HFC-245fa, HCFC-244fa, and HCFC-1223xd. This fraction was further distilled to recover recyclable components. The HFC-245fa was removed in a distillation apparatus at about 55 psia. Removal of the HCFC-244fa was accompanied throughout the entire cut by about 3.5% by weight HCFC-1223xd as an azeotrope, or azeotrope-like mixture. Following removal of this cut, a heel of substantially pure HCFC-1223xd remained.

EXAMPLE 2

The HCFC-244fa rich distillate fraction from Example 1 was re-fractionated at atmospheric pressure in a different distillation apparatus. The result was a constant-boiling distillate containing about 3.5% by weight HCFC-1223xd throughout the distillation. This occurs at a boiling point of about 41° C. While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An azeotropic or azeotropic-like composition comprising 1-chloro-1,3,3,3-tetrafluoropropane and 1,2-dichloro-3,3,3-trifluoropropene.

2. An azeotropic or azeotropic-like composition comprising from greater than about 0 weight percent to about 50 weight percent 1,2-dichloro-3,3,3-trifluoropropene and about 50 weight percent to less than about 100 weight percent 1-chloro-1,3,3,3-tetrafluoropropane.

3. The composition of claim 2 comprising from about 1 to about 50 weight percent of 1,2-dichloro-3,3,3-trifluoropropene and from about 50 to about 99 weight percent of 1-chloro-1,3,3,3-tetrafluoropropane.

4. The composition of claim 2 comprising from about 1 weight percent to about 4 weight percent of 1,2-dichloro-3,3,3-trifluoropropene and from about 96 weight percent to about 99 weight percent of 1-chloro-1,3,3,3-tetrafluoropropane.

5. The composition of claim of claim 2 comprising about 3.5 weight percent 1,2-dichloro-3,3,3-trifluoropropene and about 96.5 weight percent 1-chloro-1,3,3,3-tetrafluoropropane.

6. The composition of claim 1 wherein said composition has a boiling point of from about 41° C. to about 160° C. at a pressure of from about 14 psia to about 215 psia.

7. The composition of claim 1 wherein said composition has a boiling point of from about 41° C. to about 100° C. at a pressure of from about 15 psia to about 80 psia.

8. The composition of claim 1 wherein said composition has a boiling point of about 96.5° C. at a pressure of about 78 psia.

9. The composition of claim 8 wherein said composition comprises about 3.5% of 1,2-Dichloro-3,3,3-trifluoropropene.

10. The composition of claim 1 wherein said composition has a boiling point of about 41° C. at atmospheric pressure.

11. A process for forming an azeotropic or azeotropic-like composition of 1,2-dichloro-3,3,3-trifluoropropene and 1-chloro-1,3,3,3-tetrafluoropropane comprising the steps of:

(a) reacting hydrogen fluoride with 1,1,1,3,3-pentachloropropane thereby producing an intermediate composition; and thereafter (b) separating an azeotropic or azeotropic-like composition of 1,2-dichloro-3,3,3-trifluoropropene and 1-chloro-1,3,3,3-tetrafluoropropane from the intermediate composition.

12. The process of claim 11 comprising the steps of:

(a) reacting hydrogen fluoride with 1,1,1,3,3-pentachloropropane thereby producing an intermediate composition comprising 1,1,1,3,3-pentafluoropropane, hydrogen fluoride, hydrochloric acid, 1,2-dichloro-3,3,3-trifluoropropene and 1-chloro-1,3,3,3-tetrafluoropropane; and thereafter (b) separating 1,1,1,3,3-pentafluoropropane, hydrogen fluoride and hydrochloric acid from the intermediate composition, to thereby form an azeotropic or azeotropic-like composition of 1,2-dichloro-3,3,3-trifluoropropene and 1-chloro-1,3,3,3-tetrafluoropropane.

13. The process of claim 11 comprising the steps of:

(a) reacting hydrogen fluoride with 1,1,1,3,3-pentachloropropane, thereby producing an intermediate composition comprising 1,1,1,3,3-pentafluoropropane, hydrogen fluoride, hydrochloric acid, 1,2-dichloro-3,3,3-trifluoropropene and 1-chloro-1,3,3,3-tetrafluoropropane;

(b) removing hydrogen fluoride, hydrochloric acid and at least part of said 1,1,1,3,3-pentafluoropropane from the intermediate composition, thereby leaving a remainder;

(c) distilling the remainder to remove remaining 1,1,1,3,3-pentafluoropropane, leaving an azeotropic or azeotrope-like composition of 1-chloro-1,3,3,3-tetrafluoropropane and 1,2-dichloro-3,3,3-trifluoropropene.

14. The process of claim 13 wherein the resulting azeotropic or azeotrope-like composition comprises from about 1 percent by weight to about 4 percent by weight of 1,2-dichloro-3,3,3-trifluoropropene and from about 96 percent by weight to about 99 percent by weight of 1-chloro-1,3,3,3-tetrafluoropropane.

15. The process of claim 13 wherein said distilling is conducted at a pressure of from about 1 psia to about 250 psia.

16. The process of claim 13 wherein said distilling is conducted at a pressure of from about 15 psia to about 150 psia.

17. The process of claim 13 wherein said distilling is conducted at a pressure of from about 20 psia to about 80 psia.

18. The process of claim 13 wherein the distilling is conducted at a temperature of from about 30° C. to about 160° C.

19. The process of claim 13 wherein the distilling is conducted at a temperature of from about 35° C. to about 120° C.

20. The process of claim 13 wherein the distilling is conducted at a temperature of from about 41° C. to about 97° C.

21. An azeotropic or azeotropic-like composition consisting essentially of 1-chloro-1,3,3,3-tetrafluoropropane and 1,2-dichloro-3,3,3- trifluoropropene.

22. The composition of claim 21 consisting essentially of from greater than about 0 weight percent to about 50 weight percent 1,2-dichloro-3,3,3-trifluoropropense and about 50 weight percent to less than about 100 weight percent 1-chloro-1,3,3,3-tetrafluoropropane.

23. The composition of claim 21 consisting essentially of from about 1 to about 50 weight percent of 1,2-dichloro-3,3,3-trifluoropropene and from about 50 to about 99 weight percent of 1-chloro-1,3,3,3-tetrafluoropropane.

24. The composition of claim 21 consisting essentially of from about 1 weight percent to about 4 weight percent of 1,2-dichloro-3,3,3-trifluoropropene and from about 96 weight percent to about 99 weight percent of 1 weight percent of 1-chloro-1,3,3,3-tetrafluoropropane.

25. The composition of claim of claim 21 consisting essentially of about 3.5 weight percent 1,2-dichloro-3,3,3-trifluoropropene and about 96.5 weight percent 1-chloro-1,3,3,3-tetrafluoropropane.

26. The composition of claim 21 wherein said composition has a boiling point of from about 41° C to about 160° C at a pressure of from about 14 psia to about 215 psia.

27. The composition of claim 21 wherein said composition has a boiling point of from about 41° C to about 100° C at a pressure of from about 15 psia to about 80 psia.

28. The composition of claim 21 wherein said composition has a boiling point of about 96.5° C. at pressure of about 78 psia.

29. The composition of claim 28 wherein said composition consists essentially of about 3.5% of 1,2- Dichloro-3,3,3-trifluoropropene.

30. The composition of claim 21 wherein said composition has a boiling point of about 41° C. at atmospheric pressure.

31. A process for forming an azeotropic or axeotropic-like composition of 1,2-dichloro-3,3,3-tetrafluoropropane comprising the steps of:
 (a) reacting hydrogen fluoride with 1,1,1,1,1-pentachloropropane thereby producing an intermediate composition; and thereafter
 (b) separating an azeotropic or azeotropic-like composition consisting essentially of 1,2-dichloro-3,3,3-trifluoropropene and 1-chloro-1,3,3,3-tetrafluoropropane from the intermediate composition.

32. The process of claim 31 wherein the resulting azeotropic or azeotrope-like composition consists essentially of from greater than about 0 weight percent to about 50 weight percent 1,2-dichloro-3,3,3-trifluoropropene and about 50 weight percent to less than about 100 weight percent 1-chloro-1,3,3,3-tetrafluoropropane.

33. The process of claim 31 wherein the resulting azeotropic or azeotrope-like composition consists essentially of from about 1 percent by weight to about 4 percent by weight of 1,2-dichloro-3,3,3-trifluoropropene and from about 96 percent by weight to about 99 percent by weight of 1-chloro-1,3,3,3-tetrafluoropropane.

* * * * *